(12) United States Patent
Losordo et al.

(10) Patent No.: US 10,258,764 B2
(45) Date of Patent: Apr. 16, 2019

(54) OPENING SYSTEM FOR IMPROVING CATHETER DELIVERY

(71) Applicant: COVIDIEN LP, Mansfield, MA (US)

(72) Inventors: Michael Losordo, San Juan Capistrano, CA (US); Evan Epstein, Los Angeles, CA (US)

(73) Assignee: Covidien LP, Mansfield, MA (US)

( * ) Notice: Subject to any disclaimer, the term of this patent is extended or adjusted under 35 U.S.C. 154(b) by 445 days.

(21) Appl. No.: 14/447,539

(22) Filed: Jul. 30, 2014

(65) Prior Publication Data

US 2016/0030709 A1    Feb. 4, 2016

(51) Int. Cl.
*A61M 25/00* (2006.01)
*A61M 25/09* (2006.01)
(Continued)

(52) U.S. Cl.
CPC ... *A61M 25/0043* (2013.01); *A61B 17/12031* (2013.01); *A61B 17/12113* (2013.01); *A61B 17/12118* (2013.01); *A61M 25/00* (2013.01); *A61M 25/0009* (2013.01); *A61M 25/0102* (2013.01); *A61M 25/09* (2013.01); *A61M 29/00* (2013.01); *A61B 2017/1205* (2013.01); *A61B 2017/22042* (2013.01); *A61F 2/966* (2013.01); *A61F 2002/823* (2013.01); *A61M 2025/0019* (2013.01); *A61M 2025/0024* (2013.01);
(Continued)

(58) Field of Classification Search
CPC ...... A61B 17/3439; A61M 2025/0018; A61M 2025/0019; A61M 2025/0024; A61M 2025/0059; A61M 2025/0063; A61M 2025/0177; A61M 2025/09175; A61M 2025/09183; A61M 25/0102; A61M 25/0133; A61M 25/0152; A61M 25/0023
See application file for complete search history.

(56) References Cited

U.S. PATENT DOCUMENTS 4,020,829 A    5/1977 Willson et al.
4,027,668 A    6/1977 Dunn
(Continued)

FOREIGN PATENT DOCUMENTS

EP    0778042 A2    6/1997
EP    1958731 A1    8/2008
(Continued)

OTHER PUBLICATIONS

International Search Report and Written Opinion dated Oct. 7, 2015; International Application No. PCT/US2015/041456; 22 pages.

*Primary Examiner* — Bhisma Mehta
*Assistant Examiner* — James D Ponton
(74) *Attorney, Agent, or Firm* — Fortem IP LLP; Matthew Lincicum (57) ABSTRACT

A ball-tipped mandrel, separate or integrated on a device delivery assembly, can be used to ease delivery and/or retrieval of an ancillary device within a body vessel having tortuous anatomy. A ball-tipped mandrel can be moved through a catheter as a part of a preparation procedure prior to insertion into a body vessel of a patient. A ball-tipped mandrel can be moved through a catheter during or after insertion into a body vessel of a patient in preparation for delivery of an ancillary device. A ball-tipped mandrel can be integrated onto the distal portion of a device to produce dilation during device delivery.

8 Claims, 7 Drawing Sheets

(51) Int. Cl.
  *A61M 25/01* (2006.01)
  *A61M 29/00* (2006.01)
  *A61B 17/12* (2006.01)
  A61F 2/966 (2013.01)
  A61F 2/82 (2013.01)
  A61B 17/22 (2006.01)

(52) U.S. Cl.
  CPC ........... *A61M 2025/0025* (2013.01); *A61M 2025/0042* (2013.01); *A61M 2025/0059* (2013.01); *A61M 2025/0063* (2013.01); *A61M 2210/12* (2013.01)

(56) References Cited

U.S. PATENT DOCUMENTS

| | | | |
|---|---|---|---|
| 4,215,703 A | 8/1980 | Willson | |
| 4,381,013 A | 4/1983 | Dutcher | |
| 4,610,671 A | 9/1986 | Luther | |
| 4,834,709 A * | 5/1989 | Banning | A61M 25/0041 604/170.02 |
| 5,042,475 A | 8/1991 | LaBombard | |
| 5,059,176 A | 10/1991 | Winters | |
| 5,125,902 A | 6/1992 | Berry et al. | |
| 5,176,637 A | 1/1993 | Sagae | |
| 5,334,168 A | 8/1994 | Hemmer | |
| 5,382,238 A * | 1/1995 | Abrahamson | A61M 25/0102 600/434 |
| 6,090,072 A | 7/2000 | Kratoska et al. | |
| 6,245,029 B1 | 6/2001 | Fujita et al. | |
| 6,613,038 B2 | 9/2003 | Bonutti et al. | |
| 6,652,491 B1 | 11/2003 | Walker et al. | |
| 7,144,386 B2 | 12/2006 | Korkor et al. | |
| 8,562,573 B1 | 10/2013 | Fischell | |
| 2001/0039412 A1 | 11/2001 | Fariabi | |
| 2003/0065353 A1 | 4/2003 | Horzewski et al. | |
| 2004/0019322 A1 | 1/2004 | Hoffmann | |
| 2005/0059931 A1 * | 3/2005 | Garrison | A61M 25/10 604/101.04 |
| 2005/0171493 A1 | 8/2005 | Nicholls | |
| 2008/0281228 A1 * | 11/2008 | Parodi | A61M 25/09 600/585 |
| 2009/0264833 A1 | 10/2009 | Boyle, Jr. | |
| 2011/0098663 A1 | 4/2011 | Zinn | |
| 2011/0152763 A1 | 6/2011 | Bishop et al. | |
| 2012/0041308 A1 * | 2/2012 | Yanuma | A61M 25/0068 600/435 |
| 2013/0030369 A1 | 1/2013 | Root et al. | |
| 2013/0331819 A1 * | 12/2013 | Rosenman | A61M 25/0045 604/510 |
| 2014/0025085 A1 | 1/2014 | Zhou et al. | |
| 2015/0099936 A1 * | 4/2015 | Burdulis | A61M 25/0194 600/204 |

FOREIGN PATENT DOCUMENTS

| | | | |
|---|---|---|---|
| EP | 2027882 A1 | 2/2009 | |
| WO | WO 2014/190373 A1 * | 12/2014 | ............ A61M 19/00 |

* cited by examiner

OPENING SYSTEM FOR IMPROVING CATHETER DELIVERY

FIELD

The subject technology generally relates to catheters for use in a body vessel.

BACKGROUND

Catheters, including microcatheters, are generally tubes inserted into the body through, for example a blood vessel, and have a variety of uses. Catheters generally have a proximal end, a distal end, and at least one lumen extending from the proximal to the distal end. Catheters can be used to deliver fluids, intraluminal devices such as stents, and/or other materials to a target location or locations inside the human body. Catheters suitable for a wide variety of applications are available commercially.

SUMMARY

An aspect of at least one of the embodiments described herein includes the realization that small, flexible catheters often deform and/or collapse within the tortuous pathways of the human anatomy, in particular the human neurovasculature. This is due to the fact that such catheters, and especially the intermediate and/or distal ends of such catheters, often bend, twist, and/or become entangled within the neurovasculature during medical procedures. This unwanted bending, twisting, and/or collapsing over the catheter can make it difficult to deliver intraluminal devices through a lumen of a catheter to specific locations in the human anatomy, such as for example an aneurysm in the neurovasculature.

It would thus be desirable to provide a catheter with capability of avoiding or overcoming such deformities to facilitate smooth and accurate delivery of fluids or intraluminal devices to specific target locations in body.

Therefore, in accordance with at least one embodiment, a method of treating a catheter, can include: moving an enlarging member of an expander longitudinally within a lumen of a catheter, while the catheter is outside a patient, wherein an outer cross-sectional dimension of the enlarging member is (i) between 0.0002" and 0.0006" larger than a first inner cross-sectional dimension of the lumen in an unrestrained condition and/or (ii) between 1% and 3% larger than the first inner cross-sectional dimension of the lumen.

The method can further include inserting the catheter into a body vessel of a patient. The inserting can occur within 1 day after the moving. The inserting can occur within 1 hour after the moving. The moving can include passing the enlarging member from a first location distal to a distal end of the catheter to a second location proximal to a proximal end of the catheter.

In accordance with at least one embodiment, a system for treating a catheter, can include: a catheter having a lumen with an inner cross-sectional dimension; and an expander comprising an enlarging member having an outer cross-sectional dimension; wherein an outer cross-sectional dimension of the enlarging member is (i) between 0.0002" and 0.0006" larger than a first inner cross-sectional dimension of the lumen in an unrestrained condition and/or (ii) between 1% and 3% larger than the first inner cross-sectional dimension of the lumen.

The enlarging member can be positioned distal to a distal end of the catheter. The core wire can extend from the enlarging member to a location proximal to a proximal end of the catheter.

In accordance with at least one embodiment, a method of treating a catheter, can include: inserting a catheter into a body vessel of a patient; and moving an enlarging member of an expander longitudinally within a lumen of the catheter, while the catheter is within the body vessel, wherein an outer cross-sectional dimension of the enlarging member is (i) between 0.001" and 0.002" smaller (or between 0.0002" and 0.002" smaller) than a first inner cross-sectional dimension of the lumen in an unrestrained condition and/or (ii) between 10% and 20% smaller (or between 2% and 20% smaller) than the first inner cross-sectional dimension of the lumen.

Before inserting the catheter, the expander can be advanced to a target location within the body vessel. The inserting can include advancing the catheter over a core wire of the expander to the target location. The moving can include passing the enlarging member from a first location distal to a distal end of the catheter to a second location proximal to a proximal end of the catheter. The inserting can include forming a collapsed section of the catheter where the lumen has a second inner cross-sectional dimension less than the first inner cross-sectional dimension. The moving can include expanding the collapsed section of the catheter to have a third inner cross-sectional dimension greater than the second inner cross-sectional dimension.

The lumen can have a circular cross-sectional shape in the unrestrained condition. The inserting can include forming a collapsed section of the catheter where the lumen has a non-circular cross-sectional shape that is more eccentric than the circular cross-sectional shape. The moving can include expanding the collapsed section of the catheter to have a third inner cross-sectional shape that is less eccentric than the non-circular cross-sectional shape.

In accordance with at least one embodiment, a system for treating a catheter, can include: a catheter having a lumen with an inner cross-sectional dimension; and an expander comprising an enlarging member having an outer cross-sectional dimension; wherein an outer cross-sectional dimension of the enlarging member is (i) between 0.001" and 0.002" smaller (or between 0.0002" and 0.002" smaller) than a first inner cross-sectional dimension of the lumen in an unrestrained condition and/or (ii) between 10% and 20% smaller (or between 2% and 20% smaller) than the first inner cross-sectional dimension of the lumen.

The enlarging member can be positioned distal to a distal end of the catheter. The core wire can extend from the enlarging member to a location proximal to a proximal end of the catheter.

In accordance with at least one embodiment, treatment prior to insertion of a catheter can be combined with treatment after insertion of a catheter to further enhance delivery characteristics.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology can be practiced without some of these specific details. In other instances, well-known structures and techniques have not been shown in detail so as not to obscure the subject technology.

Delivery force is a critical factor in the usability of a stent or flow diverter in vasculature. Lower forces provide the user with more control and enhanced ability to reach tortuous locations. According to some embodiments of the subject technology, a ball or ball-tipped mandrel, separate or integrated on a device delivery assembly, can be used to ease delivery and/or retrieval of an ancillary device.

Embodiments of the subject technology can create the necessary patency and inner cavity through a part of the delivery system, thereby make existing catheters that can ovalize or become kinked during storage or delivery better able to deliver stents, flow diverters, and other devices that benefit from a high level of lumen patency. Embodiments of the subject technology improve the shape and structure of a catheter lumen, as initially positioned, for delivering ancillary devices that are delivered through a catheter. Embodiments of the subject technology can improve the usability of existing devices with relatively little development or training effort, with broad applicability to a wide variety of systems.

An aspect of at least one of the embodiments described herein includes the realization that treatment of a catheter by an enlarging member prior to delivery within a body vessel or after delivery within a body vessel improves characteristics of the catheter. An aspect of at least one of the embodiments described herein includes the realization that treatment of a catheter by an enlarging member while within a body vessel can remedy kinks, bends, and ovalization of a catheter in tortuous anatomy. (As used herein, "enlarge" and derivatives thereof, and "expand" and derivatives thereof, and "dilate" and derivatives thereof, include reshaping a cross-sectional shape of a catheter, for example where a catheter cross section is changed from a more oval to a less oval cross section, even though certain aspects of the cross-sectional shape may be reduced in size or unchanged as a result.)

An aspect of at least one of the embodiments described herein includes the realization that delivery force of a device can be reduced substantially by introduction of a mandrel with a ball welded or otherwise attached to the end of the mandrel into the inner diameter of the catheter prior to insertion of the catheter into tortuous anatomy. In this embodiment, the ball welded to the mandrel can be sized slightly larger than the inner diameter of the catheter.

An aspect of at least one of the embodiments described herein includes the realization that delivery force of a device can be reduced substantially by introduction of a mandrel with a ball welded or otherwise attached to the end of the mandrel into the inner diameter of a catheter after insertion of the catheter into tortuous anatomy. In this embodiment, the ball welded to the mandrel can be sized to or slightly smaller than the inner diameter of the catheter.

Figure 1:
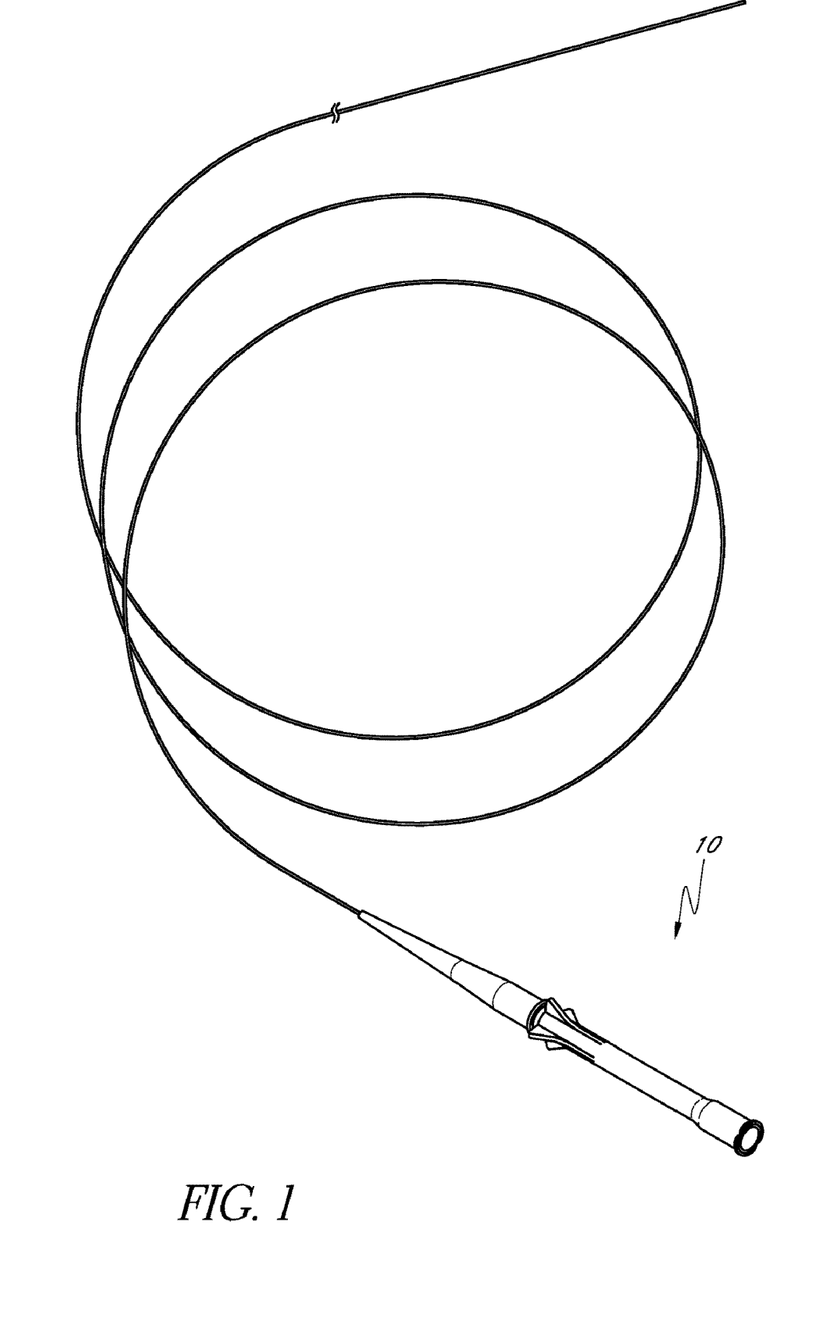
FIG. 1 shows a perspective view of an embodiment of a catheter.

According to some embodiments, as shown in FIG. 1, a catheter 10 is generally constructed to track over a conventional guidewire (or otherwise be advanced) in body vessels such as blood vessels (e.g., cervical anatomy and cerebral vessels associated with the brain). The catheter 10 can be configured to be introduced and advanced through the vasculature of the patient. The catheter 10 can comprise, for example, a microcatheter such as any of several standard designs that are generally available. Accordingly, in some embodiments the catheter 10 has a length that is at least 125 cm long, and more particularly can be between about 125 cm and about 175 cm long. In other embodiments, the catheter 10 is about 155 cm long. Inner lumen 22 of the catheter 10 in some embodiments has an inner diameter between about 0.01 inch and about 0.098 inch (0.25-2.49 mm). Other designs and dimensions are contemplated.

According to some embodiments, the catheter 10 can be an elongate tube made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other polymer coating or surface modification. Additionally, either surface can be coated with various combinations of different materials, depending upon the desired results.

Commercially available microcatheters which can be suitable for use include the MARKSMAN™ Catheter, which is available from Covidien LP, the REBAR™ Reinforced Micro Catheter, which is available from Covidien LP, the TURBOTRAKER™ catheter, which is available from Target Therapeutics, Inc., and the RAPIDTRANSIT™ catheter available from Cordis Endovascular Corporation.

The catheter 10 can be packaged by itself, with other catheters, or with other components, as described further herein. For example, a package or kit can contain a single catheter 10, for single use (e.g., disposable), or can include the catheter 10, a guidewire, and a delivery catheter that carries a stent or suitable vascular device or occluding device as described elsewhere herein. The catheter 10 can be packaged in a packaging hoop, or other suitable packaging.

Figure 2:
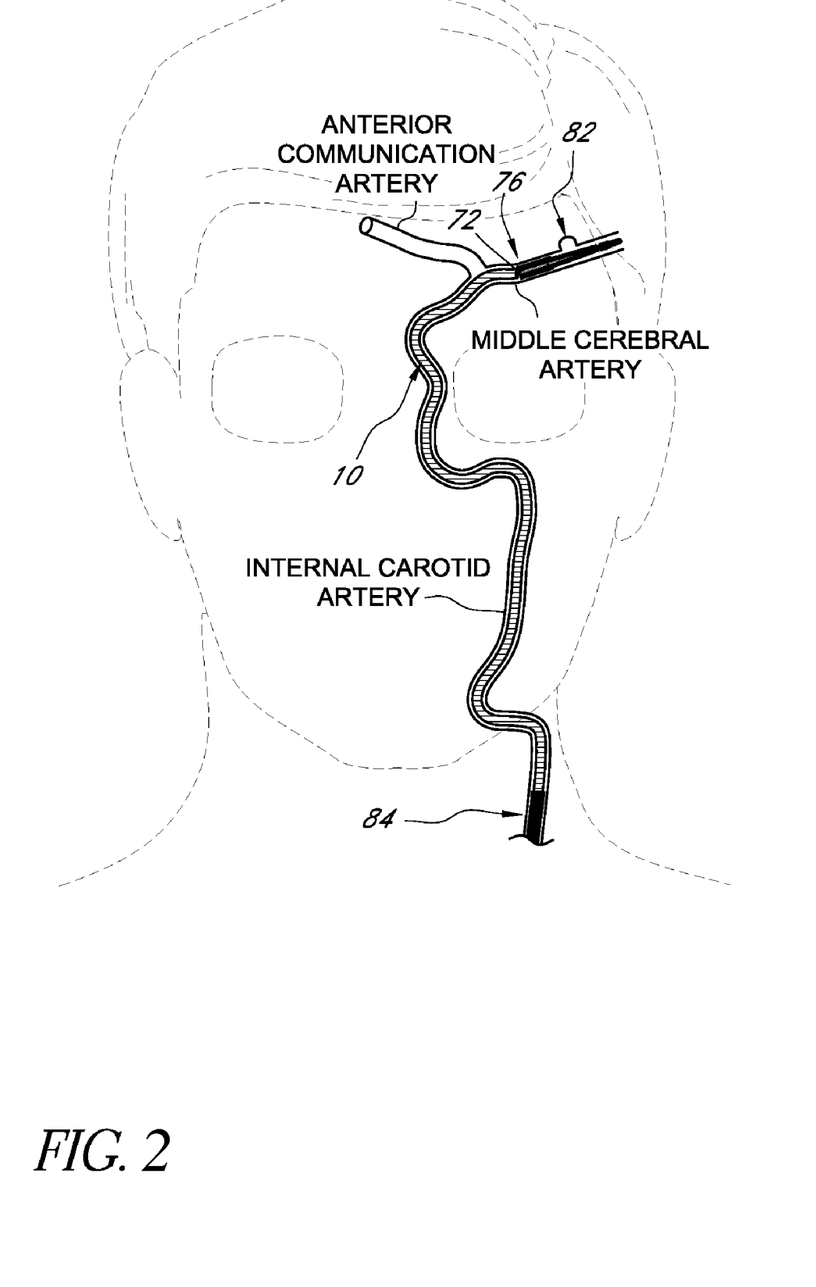
FIG. 2 shows an enlarged view of an embodiment of a catheter delivering an occluding device delivery system near an aneurysm.

As shown in FIG. 2, a guidewire and catheter 10 can be advanced (optionally through a guiding catheter 84) to a selected target site in the human anatomy by alternately advancing the guidewire and then tracking the catheter 10 over the guidewire. Fluid, a vascular device, a vascular device delivery system, or some other material can then be inserted through the lumen 22 of the catheter 10. For example, systems such as those described in U.S. Patent Publication No. 2006/0271149, U.S. Patent Publication No. 2006/0271153, U.S. Patent Publication No. 2009/0318947, U.S. Pat. No. 6,679,893, U.S. Patent Publication No. 2008/0269774, U.S. Patent Publication No. 2013/0304185, U.S. Pat. No. 8,591,566, U.S. Patent Publication No. 2011/006021, and U.S. Pat. No. 8,632,584, the entirety of each of which is hereby incorporated by reference, can be inserted through the lumen 22 of catheter 10 and delivered to the tip 72.

FIG. 2 illustrates embodiments of the catheter 10 being used to deliver a vascular device delivery system 76. The occluding device delivery system 76 can include an expandable vascular device 78, such as a stent, configured to be released at a target location 82, for example, and can be used to occlude blood flow into an aneurysm. The target location 82 (e.g. aneurysm) can be located at various locations in the human body. For example, in some embodiments an aneurysm can be located within at least one branch of the middle cerebral artery as shown in FIG. 2. The catheter 10 can be used to reach target locations (e.g. aneurysms) located elsewhere in the body as well, include but not limited to other arteries, branches, and blood vessels, such as arteries associated with the liver, and with the back of the head.

Figure 3:
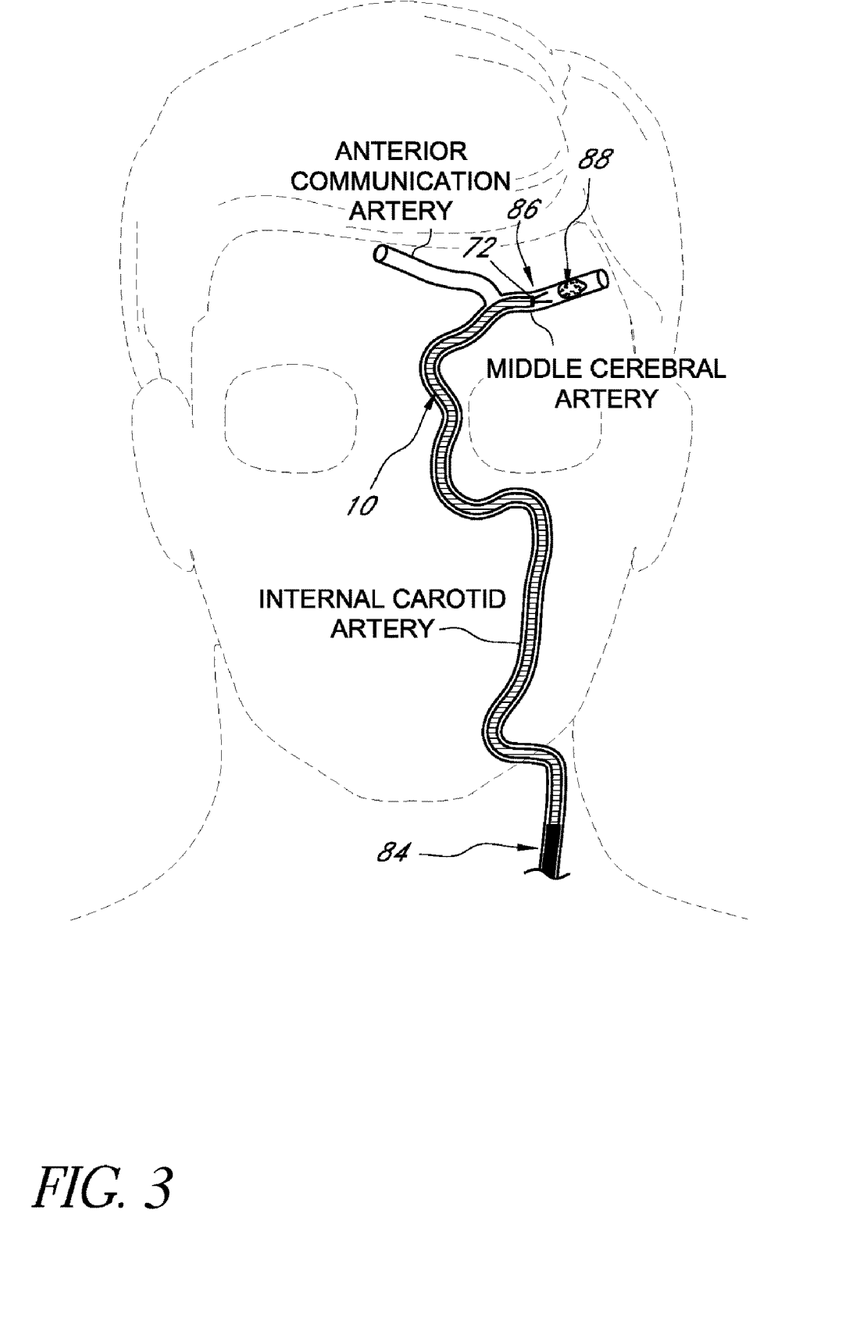
FIG. 3 shows a schematic illustration of an embodiment of a catheter, showing delivery of a clot retrieval device to a clot in the neurovasculature.

Similarly, as shown in FIG. 3, a clot retrieval device (e.g. a stentriever such as that described in U.S. Pat. No. 6,679,893 and U.S. Publication No. 2008/0269774, the entirety of each of which is hereby incorporated by reference) can be inserted through the lumen 22 of catheter 10 and delivered to the tip 72.

FIG. 3 illustrates an embodiment of the catheter 10 being used to deliver a clot retrieval device to remove a clot in the neurovasculature of the human brain. The catheter 10 can be delivered (optionally through a guiding catheter 84) into the target vessel, e.g. the internal carotid artery. The catheter 10 can be advanced until its distal tip 72 enters the middle cerebral artery, passes through the clot 88 and is located just beyond the distal end of the clot. As illustrated in FIG. 3, a clot retrieval device 86 can be delivered through the catheter 10 to the location of the clot, and the catheter 10 retracted proximally by a distance sufficient to unsheath the device 86 which then expands into the clot 88. The clot retrieval device 86 thus grabs hold of the clot 88 and can be used to pull the clot 88 back towards the catheter 10, or into the guiding catheter 84 for removal.

Figure 4A:
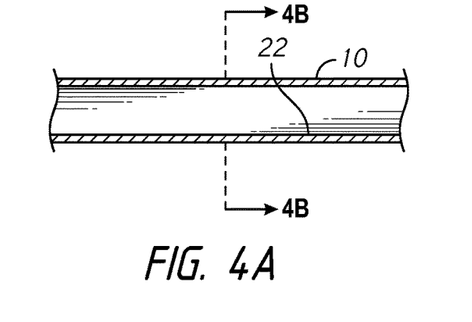
FIG. 4A shows a cross-sectional view of an embodiment of a catheter in a natural condition.
Figure 4B:
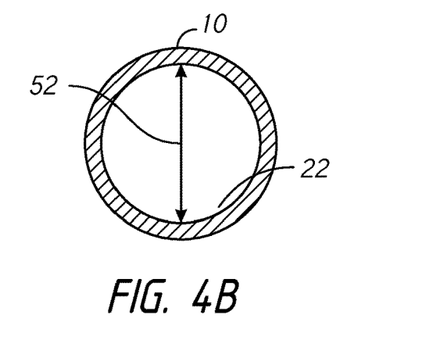
FIG. 4B shows a cross-sectional view of an embodiment of the catheter of FIG. 4A.
Figure 5A:
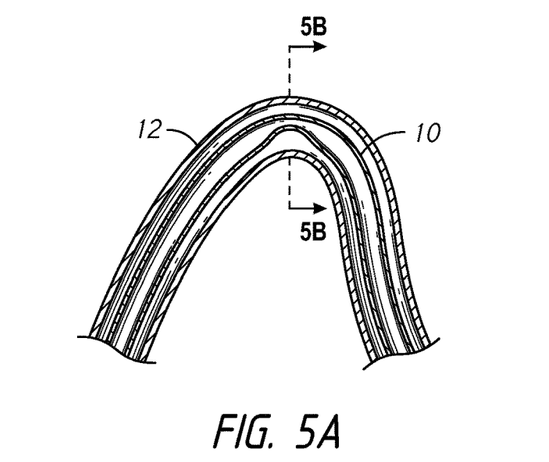
FIG. 5A shows a partial sectional view of an embodiment of a catheter in a body vessel having tortuous anatomy.
Figure 5B:
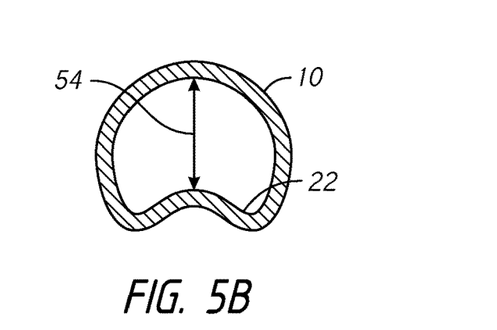
FIG. 5B shows a cross-sectional view of an embodiment of the catheter of FIG. 5A.
Figure 6A:
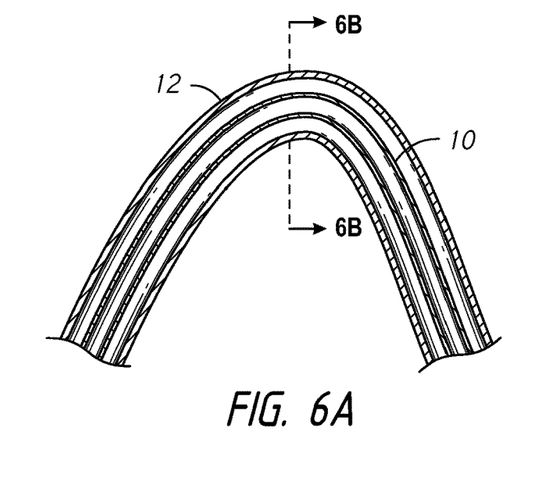
FIG. 6A shows a partial sectional view of an embodiment of a catheter in a body vessel having tortuous anatomy.
Figure 6B:
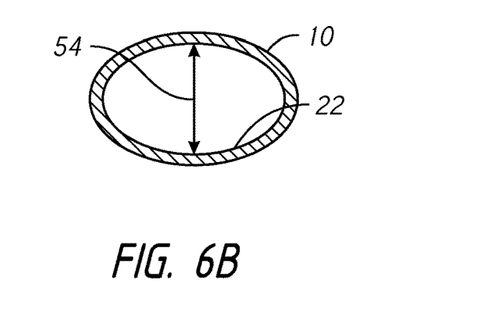
FIG. 6B shows a cross-sectional view of an embodiment of the catheter of FIG. 6A.

As the catheter 10 is deployed within a body vessel 12 having tortuous anatomy, a lumen 22 defined by the catheter 10 may undergo various changes. As shown in FIG. 4A-B, a lumen 22 can have a circular cross-sectional profile with a nominal (i.e., unrestrained such as when the catheter 10 is in a generally straight and/or unstressed configuration) diameter 52 in a relaxed state. As shown in FIGS. 5A-6B, an inner diameter of the lumen 22 of the catheter 10 is decreased in some areas along the length of the catheter 10. In some instances, as shown in FIGS. 5A-B, the catheter 10 can undergo kinking around the ends of the body vessel, whereby the catheter 10 folds, such that one side of the cross-sectional dimension collapses toward an initial center of the lumen 22. In some instances, as shown in FIGS. 6A-B, the lumen 22 can undergo ovalization when implanted within a body vessel, whereby the circular cross-sectional profile deforms to an oval cross-sectional profile. In such instances, the collapsed diameter 54 of the lumen 22 is decreased in at least one axis of the cross-sectional profile. Such a condition limits or constrains the space for advancement and delivery of devices within the lumen 22 of the catheter 10.

Figure 7:
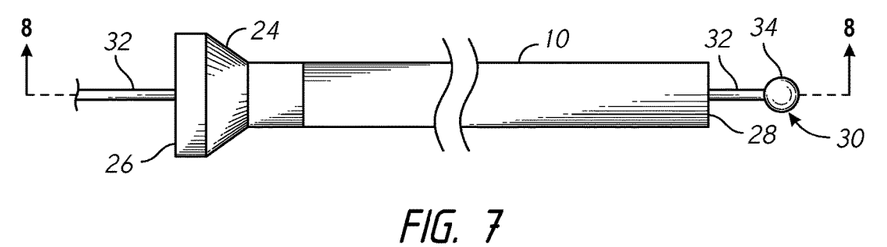
FIG. 7 shows a schematic illustration of an embodiment of a catheter and an expander extending through the catheter.
Figure 8:
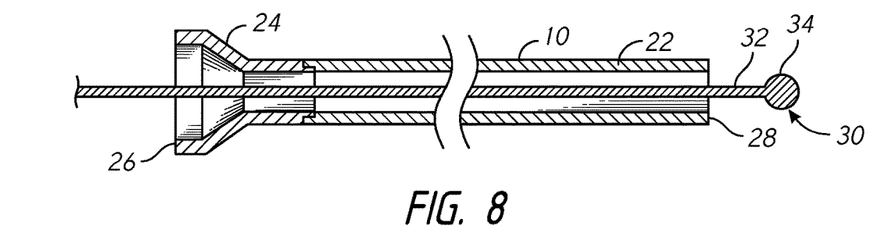
FIG. 8 shows a cross-sectional view of an embodiment of a catheter and an expander extending through the catheter.
Figure 9:
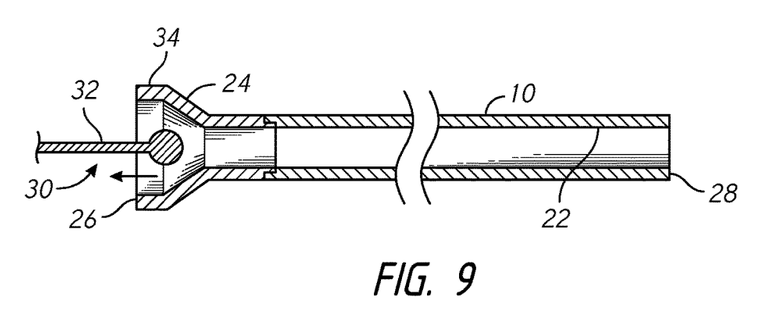
FIG. 9 shows a cross-sectional view of an embodiment of a catheter and an expander retracted proximally through the catheter.

According to some embodiments, an enlarging and/or shaping member such as a ball-tipped mandrel can be moved through a catheter as a part of a preparation procedure prior to (and/or after) insertion into a body vessel of a patient. According to some embodiments, as shown in FIGS. 7-9, a system of the subject technology includes a catheter 10 having a lumen 22 with an inner cross-sectional profile. An expander 30 is provided within at least a portion of the lumen 22 of the catheter 10. For example, as shown in FIG. 8, the expander 30 includes a control wire 32 extending through the lumen 22 and an enlarging member 34 at or near a distal end 28 of the control wire 32. The enlarging member 34 of the expander 30 can be initially provided distal to a distal end 28 of the catheter 10 and the lumen 22 thereof.

According to some embodiments, a system and method are provided for treating a catheter 10 prior to insertion within a body vessel 12. According to some embodiments, a system for treating a catheter 10 can include a catheter 10 having a lumen 22 with an inner cross-sectional dimension. The system can further include an expander 30 having an enlarging member 34 with an outer cross-sectional dimension. The system can be provided as a kit or as part of a kit to be utilized prior to positioning within a body vessel 12. For example, the catheter 10 can be provided in a kit with the expander 30 extending through a lumen 22 of the catheter 10 with a control member, shaft or wire 32. According to some embodiments, the enlarging member 34 of the expander 30 can be positioned distal to a distal end 28 of the catheter 10 and/or the lumen 22. According to some embodiments, the control shaft or wire 32 of the expander 30 extends from the enlarging member 34 to a location proximal to a proximal end 26 of the catheter 10. For example, the control wire 32 can be accessible to a user of the system.

Alternatively, the catheter 10 and the expander 30 can be provided separately in a kit and subsequently arranged as described above.

According to some embodiments, the enlarging member 34 of the expander 30 can comprise a rigid structure. For example, the enlarging member 34 can be of a metal material and/or a rigid polymer. Enlarging member 34 can be attached to or integrally formed with the control wire 32 of the expander 30.

According to some embodiments, the enlarging member 34 can form a sphere. Alternatively, according to some embodiments, the enlarging member 34 can form one or more of a variety of shapes. For example, the enlarging member 34 can form a sphere, prolate spheroid, hemisphere, ovoid, cone, frustum cone, cylindrical, bullet and/or tapered shape. According to some embodiments, the enlarging member 34 can include a combination of shapes. According to some embodiments, the enlarging member 34 can form a shape that has a varying cross-sectional dimension. For example, the cross-sectional shape of the enlarging member 34 can increase from a first cross-sectional dimension at a proximal end thereof to a second cross-sectional dimension, greater than the first cross-sectional dimension, at a distal end thereof.

According to some embodiments, an outer cross-sectional dimension of the enlarging member 34 can be larger than a nominal inner cross-sectional dimension of the lumen 22 in an unrestrained condition to provide an expansive force upon the catheter 10 when traveling through the lumen 22. For example, the outer cross-sectional dimension of the enlarging member 34 can be between 0.0002" and 0.0006" larger than the nominal inner cross-sectional dimension of the lumen 22 in an unrestrained condition. It will be appreciated that the outer cross-sectional dimension of the enlarging member 34 can be about 0.00001", 0.0001", 0.0002", 0.0003", 0.0004", 0.0005", 0.0006", 0.0007", 0.0008", 0.0009", or 0.0010" (or within a range between any two of the foregoing) larger than the nominal inner cross-sectional dimension of the lumen 22 in an unrestrained condition. According to some embodiments, the outer cross-sectional dimension of the enlarging member 34 can be between 1% and 3% larger than the nominal inner cross-sectional dimension of the lumen 22 in an unrestrained condition. It will be appreciated that the outer cross-sectional dimension of the enlarging member 34 can be about 0.1%, 0.5%, 1.0%, 1.5%, 2.0%, 2.5%, 3.0%, 3.5%, 4.0%, 4.5%, or 5.0% (or within a range between any two of the foregoing) larger than the nominal inner cross-sectional dimension of the lumen 22 in an unrestrained condition.

According to some embodiments, as shown in FIGS. 8-9, while the catheter 10 is outside a body vessel 12 of a patient, the enlarging member 34 of the expander 30 can be moved longitudinally within the lumen 22 of the catheter 10. The enlarging member 34 can be moved from a first location distal to a distal end 28 of a catheter 10 to a second location proximal to a proximal end 26 (e.g., handle 24) of the catheter 10. For example, the expander 30 can be moved toward a user, such that the enlarging member 34 passes through an entire length of the catheter 10. Alternatively, the expander 30 can be moved such that the enlarging member 34 passes through only a portion of the catheter 10, for example, through a distal portion, middle portion, and/or a proximal portion of the catheter 10.

According to some embodiments, the treated catheter 10 can be inserted into a body vessel 12 of a patient after treatment by the expander 30. For example, the treated catheter 10 is inserted into the body vessel 12 and delivered to a target region. The inserting can occur within a given time period after treatment by the expander 30. For example, the inserting can occur within one hour, two hours, three hours, four hours, five hours, six hours, one day, two days, three days, four days, five days, six days, one week, or two weeks (or within a range between any two of the foregoing) after the treatment by the expander 30.

According to some embodiments, as the treated catheter 10 is inserted through tortuous anatomy of the body vessel 12 of a patient, the treated catheter 10 maintains an inner cross-sectional profile that more closely conforms to a natural inner cross-sectional profile in a relaxed condition. For example, a degree of eccentricity within the lumen 22 will be less than would have occurred had the catheter 10 not been treated by the expander 30 prior to insertion into the body vessel 12. According to some embodiments, the catheter 10, while within the body vessel 12, maintains a greater degree of compliance with the anatomy of the body vessel 12, such that the catheter 10 undergoes less kinking and ovalization than would have occurred had the catheter 10 not been treated by the expander 30 prior to insertion within the body vessel 12.

Figure 10:
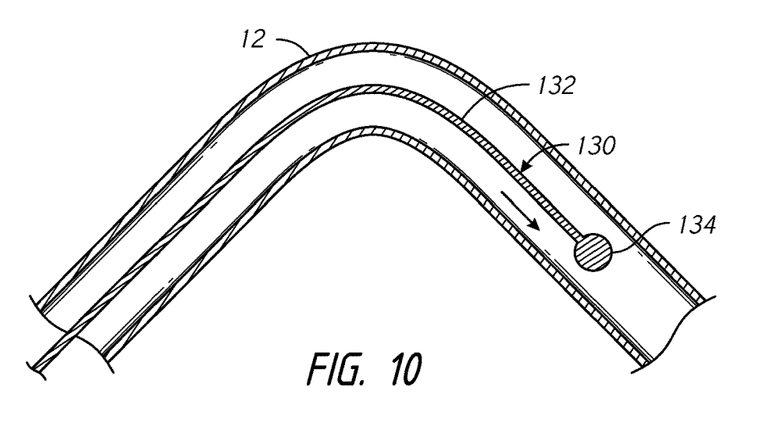
FIG. 10 shows a partial sectional view of an embodiment of an expander extending through a body vessel to a target location.
Figure 11:
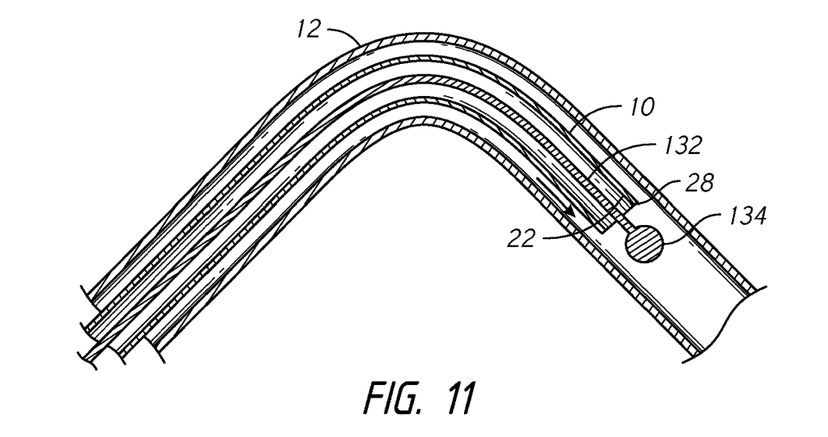
FIG. 11 shows a partial sectional view of an embodiment of a catheter extending over an expander to a target location.

According to some embodiments, an expander in the form of, for example, a ball-tipped mandrel can be moved through a catheter during or after insertion into a body vessel of a patient in preparation for delivery of an ancillary device. According to some embodiments, as shown in FIG. 10, the expander 130 is advanced to a target location within the body vessel 12 prior to advancement of the catheter 10. For example, the expander 130 can serve as a guidewire to be advanced to a target location. Subsequently, as shown in FIG. 11, the catheter 10 can be advanced along the control shaft or wire 132 of the expander 130 to arrive at or near the target location. Alternatively, according to some embodiments, expander 130 and catheter 10 are advanced together to a target location to achieve the configuration shown in FIG. 11.

According to some embodiments, an outer cross-sectional dimension of the enlarging member 134 can be smaller than a nominal inner cross-sectional dimension of the lumen 22 in an unrestrained condition to provide an expansive force upon the catheter 10 when traveling through the lumen 22. While smaller than the nominal inner cross-sectional dimension, the outer cross-sectional dimension of the enlarging member 134 is nonetheless larger than a collapsed inner cross-sectional dimension of the lumen 22 at at least one portion of the catheter 10. For example, the outer cross-sectional dimension of the enlarging member 134 can be between 0.001" and 0.002" smaller than the nominal inner cross-sectional dimension of the lumen 22 in an unrestrained condition. It will be appreciated that the outer cross-sectional dimension of the enlarging member 134 can be about 0.0001", 0.0005", 0.0010", 0.0015", 0.0020", 0.0025", 0.0030", 0.0035", 0.0040", 0.0045", or 0.0050" (or within a range between any two of the foregoing) smaller than the nominal inner cross-sectional dimension of the lumen 22 in an unrestrained condition. According to some embodiments, the outer cross-sectional dimension of the enlarging member 134 can be between 10% and 20% smaller than the nominal inner cross-sectional dimension of the lumen 22 in an unrestrained condition. It will be appreciated that the outer cross-sectional dimension of the enlarging member 134 can be about 1%, 5%, 10%, 15%, 20%, 25%, 30%, 35%, 40%, 45%, or 50% (or within a range between any two of the foregoing) smaller than the nominal inner cross-sectional dimension of the lumen 22 in an unrestrained condition.

Figure 12:
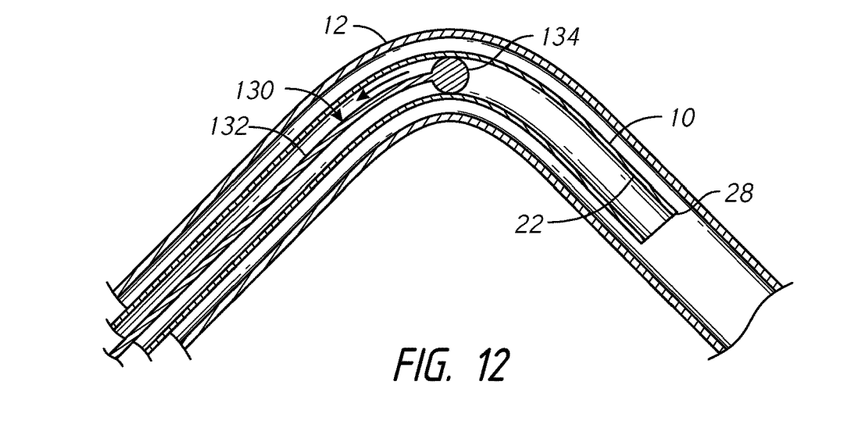
FIG. 12 shows a partial sectional view of an embodiment of a catheter and an expander retracted proximally through the catheter.

According to some embodiments, as shown in FIG. 12, once the catheter 10 and the expander 130 are delivered to a target location, with the enlarging member 134 of the expander 130 being distal to a distal end 28 of the catheter 10, the expander 130, including the enlarging member 134, can be retracted proximally, such that the enlarging member 134 is moved through the lumen 22 of the catheter 10. By such action, the enlarging member 134 is moved through portions of the lumen 22 that are located in tortuous anatomy. In such areas, the cross-sectional dimension of the lumen 22 can have collapsed, at least to some degree (e.g. by kinking or ovalization). Proximal retraction of the enlarging member 134 through the lumen 22 can restore these portions of the lumen 22 to a natural or more circular cross-sectional profile with an enlarged inner cross-sectional dimension. Accordingly, a collapsed inner cross-sectional dimension of the lumen 22, less than the nominal inner cross-sectional dimension, can be restored. Alternatively, the collapsed cross-sectional dimension can be increased to be greater than the collapsed inner cross-sectional dimension, even if the nominal inner cross-sectional dimension is not achieved. Moving the enlarging member 134 through the lumen 22 can cause a collapsed portion of the catheter 10 to transition from a shape having a first eccentricity to a shape having a second eccentricity, less than the first eccentricity. Treatment of the catheter 10 by the expander 130 can cause the catheter 10 to achieve a greater degree of compliance with the body vessel 12.

According to some embodiments, after treatment of the catheter 10 by the expander 130, devices and/or assemblies can be advanced through the lumen 22 of the catheter 10. The enlarged cross-sectional dimension of the lumen 22 achieved by the expander 130 can allow such devices and/or assemblies to travel through the lumen 22 with greater ease. According to some embodiments, after treatment of the catheter 10 by the expander 130, the catheter 10 maintains or substantially maintains its enlarged cross-sectional profile while residing within the body vessel 12.

Figure 13:
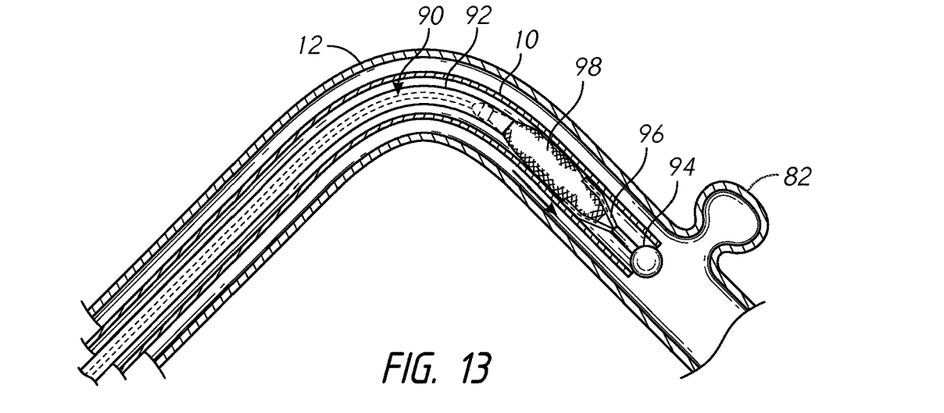
FIG. 13 shows a partial sectional view of an embodiment of a catheter and a delivery assembly extending through a body vessel to a target location.

According to some embodiments, an expander (e.g. in the form of a ball-tipped mandrel) is integrated onto the distal portion of a vascular device or vascular device delivery system to serve an opening function during device delivery. According to some embodiments, as shown in FIG. 13, the expander assembly 90 can include devices 98 and/or deployment mechanisms 96 thereon. For example, the control wire 92 of the expander assembly 90 can support an implant 98 for delivery within the body vessel 12. Such an implant can be located along the control wire 90 proximate to or distal to the enlarging member 34 of the expander 30.

According to some embodiments, an outer cross-sectional dimension of the enlarging member 94 can be smaller than a nominal inner cross-sectional dimension of the lumen 22 in an unrestrained condition to provide an expansive force upon the catheter 10 when traveling through the lumen 22. While smaller than the nominal inner cross-sectional dimension, the outer cross-sectional dimension of the enlarging member 94 can be nonetheless larger than a collapsed inner cross-sectional dimension of the lumen 22 at least one portion of the catheter 10. For example, the outer cross-sectional dimension of the enlarging member 94 can be between 0.001" and 0.002" smaller than the nominal inner cross-sectional dimension of the lumen 22 in an unrestrained condition. It will be appreciated that the outer cross-sectional dimension of the enlarging member 94 can be about 0.0001", 0.0005", 0.0010", 0.0015", 0.0020", 0.0025", 0.0030", 0.0035", 0.0040", 0.0045", or 0.0050" (or within a range between any two of the foregoing) smaller than the nominal inner cross-sectional dimension of the lumen 22 in an unrestrained condition. According to some embodiments, the outer cross-sectional dimension of the enlarging member 94 can be between 10% and 20% smaller than the nominal inner cross-sectional dimension of the lumen 22 in an unrestrained condition. It will be appreciated that the outer cross-sectional dimension of the enlarging member 94 can be about 1%, 5%, 10%, 15%, 20%, 25%, 30%, 35%, 40%, 45%, or 50% (or within a range between any two of the foregoing) smaller than the nominal inner cross-sectional dimension of the lumen 22 in an unrestrained condition.

Figure 14:
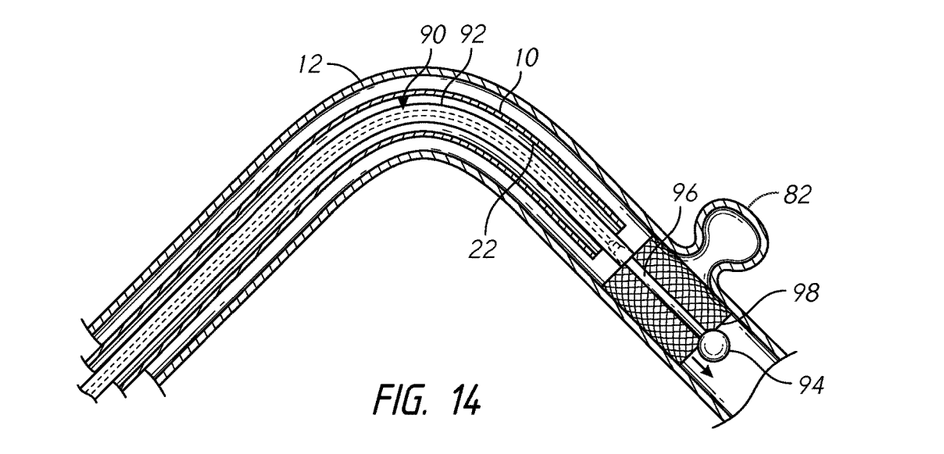
FIG. 14 shows a partial sectional view of an embodiment of a delivery assembly extending out of a catheter to deliver an implant to a target location in a body vessel.

According to some embodiments, as shown in FIG. 14, the expander assembly 90 can be advanced out of the catheter 10 to be aligned with a target location 82. A device 98 (e.g., an implant) can be deployed from a deployment mechanisms 96 of the expander assembly 90.

Figure 15:
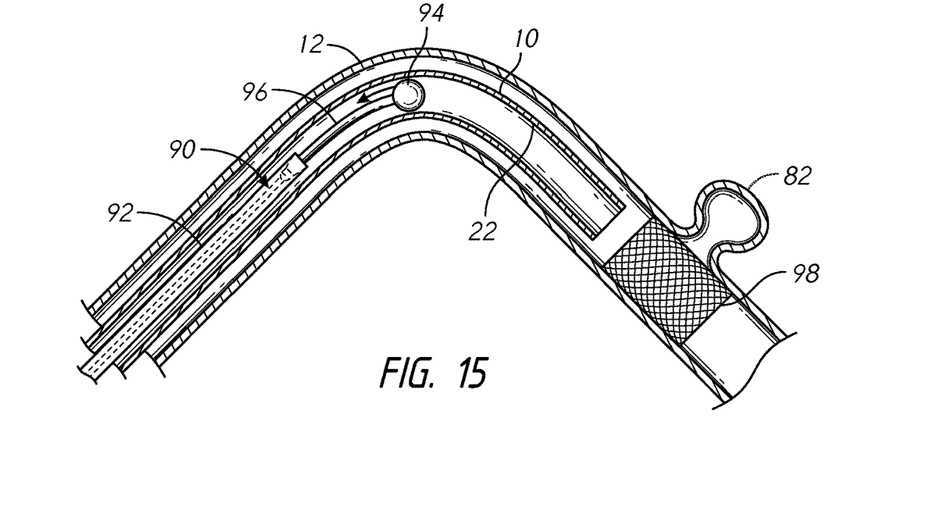
FIG. 15 shows a partial sectional view of an embodiment of a catheter and an expander of a delivery assembly retracted proximally through the catheter.

According to some embodiments, as shown in FIG. 15, once the device 98 is deployed from the deployment mechanisms 96, the expander assembly 90, including the enlarging member 94, can be retracted proximally, such that the enlarging member 94 is moved through the lumen 22 of the catheter 10. By such action, the enlarging member 94 is moved through portions of the lumen 22 that are located in tortuous anatomy. In such areas, the cross-sectional dimension of the lumen 22 can have collapsed, at least to some degree (e.g. by kinking or ovalization). Proximal retraction of the enlarging member 94 through the lumen 22 can restore these portions of the lumen 22 to a natural or more circular cross-sectional profile with an enlarged inner cross-sectional dimension. Accordingly, a collapsed inner cross-sectional dimension of the lumen 22, less than the nominal inner cross-sectional dimension, can be restored. Alternatively, the collapsed cross-sectional dimension can be increased to be greater than the collapsed inner cross-sectional dimension, even if the nominal inner cross-sectional dimension is not achieved. Moving the enlarging member 94 through the lumen 22 can cause a collapsed portion of the catheter 10 to transition from a shape having a first eccentricity to a shape having a second eccentricity, less than the first eccentricity. Treatment of the catheter 10 by the expander assembly 90 can cause the catheter 10 to achieve a greater degree of compliance with the body vessel 12.

Example 1

An investigation was performed regarding the use of an expander in a MARKSMAN™ Catheter having an unrestrained inner diameter of 0.027".

Various ball-tip mandrels with different ball diameters were inserted and advanced through the lumen of the Marksman catheters. Afterwards, a PIPELINE™ Embolization Device delivery system was used to determine the maximum delivery force required for advancement within the catheter. After each catheter was treated, a trial was performed using a plastic and glass model of human neurovasculature, including the carotid siphon. Each catheter (treated and untreated) was inserted into the vessel model. A PIPELINE Embolization Device delivery system was advanced into each inserted catheter and the maximum delivery (push) force was recorded during advancement. In one test, a first mandrel was advanced through the catheter before and after the catheter was placed in the vessel model, and a second, smaller mandrel was advanced through the catheter after the second advancement of the first mandrel.

Test 1

Expansion treatment: None
Delivery Force Max: 5.863 N

Test 2

Expansion treatment: None
Delivery Force Max: 5.376 N

Test 3

Expansion treatment: None
Delivery Force Max: 5.374 N

Test 4

Expansion treatment: None
Delivery Force Max: 5.654 N

Test 5

Expansion treatment: None
Delivery Force Max: 4.796 N

Test 6

Expansion treatment: 0.0275" OD mandrel sent through twice prior to catheter placement and testing.
Delivery Force Max: 3.226 N Test 7

Expansion treatment: 0.0275" OD mandrel sent through twice prior to catheter placement and testing.
Delivery Force Max: 3.372 N Test 8

Expansion treatment: 0.0275" OD mandrel sent through once prior to catheter placement and testing.
Delivery Force Max: 3.206 N Test 9

Expansion treatment: 0.0275" OD mandrel sent through twice prior to catheter placement and testing.
Delivery Force Max: 2.463 N Test 10

Expansion treatment: 0.0275" OD mandrel sent through twice prior to catheter placement and testing.
Delivery Force Max: 3.628 N Test 11

Expansion treatment: Mandrels run through catheter prior to testing: (1) 0.0265" OD mandrel sent through prior to catheter placement; (2) 0.0265" OD mandrel sent through in tortuosity up to syphon; (3) 0.0251" OD mandrel sent through tortuosity through syphon.
Delivery Force Max: 2.105 N As can be seen, advancing one or more mandrels through a lumen of a catheter prior to placement of the catheter in tortuous anatomy reduces the maximum delivery force required to advance an assembly within the lumen. Advancing one or more mandrels through the lumen of the catheter (up to and or through the siphon) after placement of the catheter in tortuous anatomy further reduces the maximum delivery force required to advance an assembly within the lumen. The required push force in a treated catheter can be reduced to be less than half the required push force without such treatment. Beneficial results were found when a catheter was treated both before and after insertion by differently sized mandrels.

The apparatus and methods discussed herein are not limited to treatment of a catheter for insertion into any particular vessels, but may include any number of different types of vessels. For example, in some aspects, vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

The apparatus and methods discussed herein are not limited to the deployment and use of an occluding device or stent within the vascular system but may include any number of further treatment applications. Other treatment sites may include areas or regions of the body such as organ bodies.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method of reducing forces for delivering a medical device through a catheter, comprising:
    advancing an expander distally to a target location within a body vessel of a patient, the expander comprising a control wire and an enlarging member at a distal portion of the control wire, the enlarging member having a larger cross-sectional dimension than the control wire;
    after advancing the expander, inserting a catheter over the control wire of the expander and into the body vessel, thereby forming a collapsed section of the catheter that has a non-circular cross-sectional shape; and
    after inserting the catheter, moving the enlarging member longitudinally within a lumen of the catheter in a proximal direction, while the catheter is within the body vessel, thereby expanding the collapsed section of the catheter via the enlarging member to have an inner cross-sectional shape that is more circular than the non-circular cross-sectional shape; and
    after moving the enlarging member longitudinally within the lumen of the catheter in the proximal direction, delivering a medical device distally through the catheter lumen to the target location within the body vessel of the patient,
    wherein the cross-sectional dimension of the enlarging member is between 0.0002" and 0.002" smaller than a first inner cross-sectional dimension of the lumen in an unrestrained condition.

2. The method of claim 1, wherein the cross-sectional dimension of the enlarging member is between 2% and 20% smaller than the first inner cross-sectional dimension of the lumen.

3. The method of claim 2, wherein the lumen of the catheter at the collapsed section has a second inner cross-sectional dimension less than the first inner cross-sectional dimension.

4. The method of claim 3, wherein the moving comprises expanding the collapsed section of the catheter to have a third inner cross-sectional dimension greater than the second inner cross-sectional dimension.

5. The method of claim 2, wherein the lumen has a circular cross-sectional shape in the unrestrained condition.

6. The method of claim 2, wherein the lumen has a diameter of between about 0.01 inch and about 0.098 inch.

7. The method of claim 2, wherein the lumen has a length of at least about 125 cm.

8. The method of claim 1, wherein the moving comprises passing the enlarging member from a first location entirely distal to a distal end of the catheter to a second location proximal to a proximal end of the catheter.

* * * * *